(12) United States Patent
Cohen et al.

(10) Patent No.: US 7,528,251 B2
(45) Date of Patent: May 5, 2009

(54) METHOD FOR ENANTIOSELECTIVE PREPARATION OF SULPHOXIDE DERIVATIVES

(75) Inventors: Avraham Cohen, Tel Aviv (IL); Suzy Charbit, Créteil (FR); François Schutze, Saint-Nom-la-Bretèche (FR); Frédéric Martinet, Paris (FR); Patricia Gizecki, Poitiers (FR)

(73) Assignee: Sidem Pharma SA, Luxembourg (LU)

( * ) Notice: Subject to any disclaimer, the term of this patent is extended or adjusted under 35 U.S.C. 154(b) by 0 days.

(21) Appl. No.: 11/663,647

(22) PCT Filed: Oct. 5, 2005

(86) PCT No.: PCT/FR2005/002447

§ 371 (c)(1),
(2), (4) Date: Sep. 4, 2007

(87) PCT Pub. No.: WO2006/037894

PCT Pub. Date: Apr. 13, 2006

(65) Prior Publication Data

US 2007/0299261 A1     Dec. 27, 2007

(30) Foreign Application Priority Data

Oct. 5, 2004    (FR) .................................. 04 10483

(51) Int. Cl.
*C07D 471/04*      (2006.01)

(52) U.S. Cl. .................... 546/118; 546/261; 548/303.1; 585/27

(58) Field of Classification Search ................. 546/118, 546/260, 261; 548/303.1; 585/27
See application file for complete search history.

(56) References Cited

U.S. PATENT DOCUMENTS 5,948,789 A      9/1999   Larsson et al.

FOREIGN PATENT DOCUMENTS

| WO | 03/089408 | 10/2003 |
|----|-----------|---------|
| WO | 2004/060891 | 7/2004 |
| WO | WO 2004/074285 A1 * | 9/2004 |

OTHER PUBLICATIONS

Ghosh et al., Synthesis, 1998, 937-961.*
Flores-Lopez et al., Organometallics, 2000, 19, 2153-2160.*
International Search report dated Mar. 23, 2006.

* cited by examiner

*Primary Examiner*—Bernard Dentz
*Assistant Examiner*—David E Gallis
(74) *Attorney, Agent, or Firm*—Crowell & Moring

(57) ABSTRACT

The present invention concerns enantioselective preparation of sulphoxide derivatives or their salts. The method consist in performing an enantioselective oxidation of a sulphur of general formula (I) A —$CH_2$—SB, wherein: A is a diversely substituted pyridinyl ring and B is a heterocyclic radical comprising an imidazo-pyridinyl ring, using an oxidizing agent in the presence of a titanium $^{(IV)}$-based catalyst and a chiral ligand consisting of a cyclic beta or gamma-amino-alcohol, in an organic solvent, followed, if required, by salt formation with a base. The invention is useful for preparing sulphoxides useful in therapeutics.

21 Claims, No Drawings

METHOD FOR ENANTIOSELECTIVE PREPARATION OF SULPHOXIDE DERIVATIVES

The present invention concerns a method for the enantioselective preparation of sulfoxide substituted derivatives, and more particularly, a method for the enantioselective preparation of compounds such as the enantiomers of tenatoprazole and other similar sulfoxides.

BACKGROUND OF THE INVENTION

Various sulfoxide derivatives are known, and more particularly pyridinyl-methyl-sulfinyl benzimidazoles, useful in therapeutics as drugs presenting inhibiting properties of the proton pump, that is to say drugs which inhibit the secretion of gastric acid and are useful in the treatment of gastric and duodenal ulcers. The first known derivative of the series of proton pump inhibitors is omeprazole, or 5-methoxy-2-[[(4-methoxy-3,5-dimethyl-2-pyridinyl)methyl]sulfinyl]-1H-benzimidazole described in patent EP 005.129, which possesses gastric acid secretion inhibiting properties, and is widely used as an anti-ulcerative in human therapeutics. Other derivatives of benzimidazole with similar structures are known by their generic names, for example rabeprazole, pantoprazole and lansoprazole, which all present a similar structure and can be related to the group of pyridinyl-methyl-sulfinyl-benzimidazoles.

Tenatoprazole, or 5-methoxy-2-[[(4-methoxy-3,5-dimethyl-2-pyridinyl)methyl]sulfinyl]imidazo[4,5-b]pyridine, is described in patent EP 254.588. It is also one of the drugs considered as proton pump inhibitors and can generally be used in the treatment of gastro-oesophageal reflux disease, of digestive haemorrhages, and dyspepsia. However, tenatoprazole can be structurally differentiated from the other above-mentioned proton pump inhibitors in as much as it comprises an imidazo-pyridinyl nucleus instead of a benzimidazole nucleus.

All these compounds are sulfoxides presenting an asymmetry on the sulphur atom and can therefore be under the form of a racemic mixture of two enantiomers. It may be useful to separate them selectively under the form of one or the other of the two enantiomers with R and S configurations, or (+) and (−), whose specific properties can be sensibly different. Thus, patent application No WO 2004060891 describes the S enantiomer of tenatoprazole.

Various methods have been described in the scientific literature to prepare one or the other enantiomer of these sulfoxides in a selective or preponderant manner, in particular omeprazole and its enantiomer of S configuration, esomeprazole, as well as its salts such as sodium or magnesium salts.

Thus, patent EP 652.872 describes a method for the preparation of the magnesium salt of the (−) enantiomer of omeprazole via the ester comprising a chiral acyloxymethyl group, separation of the diastereo-isomers and solvolysis in an alkaline solution. U.S. Pat. No. 5,776,765 describes a method using the stereoselective bio-reduction of a racemic mixture of sulfoxide into the corresponding sulphide, using a micro-organism comprising a DMSO reductase, and allowing for a mixture to be obtained that is highly enriched in (−) enantiomer compared to the (+) enantiomer.

H. Kagan et al., have described an asymmetric oxidation system of sulphides into sulfoxides catalysed by a complex of titanium isopropoxide and optically active diethyl tartrate, using tert-butyl hydroperoxide as an oxidizing agent in the presence of water, at a temperature lower than 0° C. [see P. Pitchen and al. J. Am. Chem. Soc. 106, pp. 8188-93 (1984)].

S. Zhao, O, Samuel and H. Kagan, Tetrahedron vol. 43, pp. 5135-44 (1987) have demonstrated that the enantioselectivity could be improved using cumene hydroperoxide under the same reaction conditions. Various variations of the method of Kagan have been developed and for example, U.S. Pat. No. 5,948,789 concerns the enantioselective preparation of various sulfoxides, and more particularly of the (−) enantiomer of omeprazole or of its sodium salts, by oxidation of the corresponding sulphide ("prochiral" sulphide) by an oxidizing agent in a particular solvent such as toluene and ethyl acetate in the presence of a base, the reaction being catalysed by a titanium complex obtained from a titanium$^{(IV)}$ compound, preferably titanium isopropoxide, and a chiral ligand chosen among aliphatic and aromatic diols, notably L(−)- or D(−)-diethyl tartrate, in presence of water. The addition of a base to the reaction medium improves the enantioselectivity of the oxidation reaction of sulphide to sulfoxide. The method described in this patent allows for a mixture to be obtained that is enriched in one or the other of the (−) and (+) enantiomers, according to the ligand used.

The above-mentioned method of Kagan, as well as its variations, makes it possible to obtain sulfoxides with a structure of the benzimidazole type, such as omeprazole and its enantiomers, easily and in an enantioselective manner. However, in the case of sulfoxides of the imidazo-pyridinyl type, the low solubility of sulphides in usual solvents such as toluene generates a heterogeneous reaction medium accompanied by a loss of selectivity and an important formation of sulfone, in the range of 30%.

More particularly, some sulphides, in particular the prochiral sulphide of tenatoprazole, are slightly soluble in the usual solvents such as toluene and methylene chloride, and the choice of the solvent often raises difficulties. Thus, it is indicated in "Asymmetric Catalysis on Industrial Scale", H. U. Blaser, E. Schmidt, 2004 Wiley-VCH Verlag GmbH & Co. KG, Grünstadt, ch. 7, p. 413, that aprotic and polar solvents have a negative influence on the asymmetric oxidation of sulphides with a pyridinyl-methyl-benzimidazole structure in catalytic systems such as those described above.

Therefore, a method able to produce sulfoxide enantiomers having an imidazole-pyridinyl structure, with a satisfactory enantiomeric excess, that would avoid the formation of sulfones, with good yield and purity conditions and being carried out in a solvent likely to be implemented on an industrial scale and presenting acceptable productivity levels, would be desirable.

SUMMARY OF THE INVENTION

The studies carried out by the applicant have shown that the enantiomers of sulfoxide derivatives, and in particular of tenatoprazole and of sulfoxides with similar structures, can be prepared with an excellent enantiomeric excess and with a good yield by enantioselective oxidation of the corresponding prochiral sulfoxide, in the presence of a specific titanium-based complex, without it being necessary to add a base to the reaction medium.

The present invention therefore relates to a method for the enantioselective preparation of sulfoxide derivatives, and of their salts, presenting an asymmetry on their sulphur atom, producing one or the other of the enantiomers with a good selectivity and a satisfactory yield.

DETAILED DESCRIPTION OF THE PREFERRED EMBODIMENTS

The invention particularly concerns a preparation method producing the (−) enantiomer, the (+) enantiomer, and their salts, in a substantially enantioselective manner. The words "in a substantially enantioselective manner" used here mean that the desired enantiomer is obtained selectively or in predominant quantity compared to the other enantiomer, that is to say that the enantiomeric excess is higher than or equal to 90%, preferably higher than 95% and more particularly higher than 98%.

According to the method of the invention, an enantioselective oxidation of a sulphide of the following general formula (I) is carried out:

A—CH$_2$—S—B (I)

wherein A is a pyridinyl nucleus diversely substituted and B a heterocyclic residue comprising an imidazo-pyridinyl nucleus, using an oxidizing agent in the presence of a titanium$^{(IV)}$-based catalyst and a chiral ligand comprising a cyclic beta- or gamma-amino-alcohol, in an organic solvent, followed as necessary by a salification by a base.

In the above general formula (I), A preferably represents a pyridinyl group or a pyridinyl group having one or several substituents selected from linear or branched alkyl groups of 1 to 6 carbon atoms, linear or branched alkoxy groups of 1 to 6 carbon atoms, methyl or ethyl groups substituted by one or several halogen atoms, amino, alkylamino or dialkylamino groups where the alkyl moiety, linear of branched, comprises 1 to 5 carbon atoms; B represents a imidazo-[4,5-b]-pyridinyl heterocycle, substituted as necessary by one or several linear of branched alkyl groups of 1 to 6 carbon atoms, linear or branched alkoxy groups of 1 to 6 carbon atoms, and preferably substituted on one or several carbons by a methyl, ethyl, methoxy or trihalogenomethyl group.

In the above general formula (I), A is preferably a 2-pyridinyl group substituted by one or several methyl, ethyl, methoxy or trifluoromethyl groups, and more particularly a 4-methoxy-3,5-dimethyl-2-pyridinyl group. B is preferably a 5-methoxy-imidazo-[4,5-b]-pyridinyl group.

Within the present invention, "cyclic beta- or gamma-amino-alcohol", means a compound comprising an amino, or imino group, and a hydroxyl group or derivative, these two groups being in beta or gamma position one compared to the other, and carried by a non aromatic nucleus itself being able to be fused with another nucleus and possibly comprising one or several heteroatoms.

A sulfoxide of general formula

A—CH$_2$—SO—B (Ia)

is therefore obtained where A and B have the above-mentioned definitions.

The starting prochiral sulfoxide represented by the above formula (I) is a known product which can be prepared using various methods described in the literature and for example the methods described in patents EP 254.588 and EP 103.553.

The oxidizing agent used in the method of the invention is preferably a hydroperoxide, for example cumene or tert-butyl hydroperoxide. According to a preferred implementation of the method, cumene hydroperoxide is used. According to an alternative, hydrogen peroxide at high concentrations, at least 30%, or hydrogen peroxide complexed by urea (UHP or "urea hydrogen peroxide" H$_2$NCONH$_2$.H$_2$O$_2$), here-after also referred to as UHP, can be used as an oxidizing agent. As indicated later, the presence of water reduces the selectivity, but this drawback can be at least partly compensated for by the addition in the reaction medium of a usual dehydrating agent such as magnesium or sodium sulphate, or an appropriate molecular sieve.

The titanium-based catalyst is an important element of the method of the invention which contributes to the reaction and allows for the desired derivative to be obtained with good yield. According to the invention, a catalyst such as a titanium$^{(IV)}$ complex, like titanium alkoxide, for example titanium$^{(IV)}$ isopropoxide Ti(OiPr)$_4$ or titanium acetyl-acetonate is preferably used. Such appropriate titanium-based catalysts are described in the literature and are available on the market.

The choice of the ligand is another characteristic-feature of the method of the invention as it is a chirality inducer; it selectively directs the reaction towards the desired enantiomer. Besides, it conditions the chemo-selectivity of the reaction.

According to the method of the invention, the ligand is a cyclic beta- or gamma-amino-alcohol which can be represented by the following general formula (II):

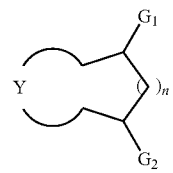

II in which G$_1$ represents an amino group —NR$_1$R$_2$ or an imino group —N═CR$_1$R$_2$ and G$_2$ represents an —OR$_3$ group, or the reverse; n equals 0 or 1; R$_1$ and R$_2$, identical or different, independently from one another, represent a hydrogen atom or a linear or branched alkyl group of 1 to 6 carbon atoms or an aryl, heteroaryl, acyl or sulfonyl group, R$_3$ represents a hydrogen atom, or a linear or branched alkyl group of 1 to 6 carbon atoms or an aryl or heteroaryl group, and Y is a cyclic residue.

The cyclic amino-alcohol of formula (II) may preferably be a derivative of the following formula (III):

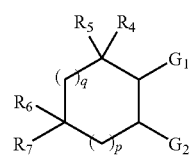

III in which G$_1$ and G$_2$ have the above mentioned definitions; p and q, identical or different, are equal to 0, 1 or 2; R$_4$, R$_5$, R$_6$ and R$_7$, identical or different, represent a hydrogen atom or a linear of branched alkyl group of 1 to 6 carbon atoms, R$_4$ and R$_6$, and/or R$_5$ and R$_7$, being able to form together an aliphatic, aromatic of heteroaryl cycle, and R$_5$ and R$_7$ being able to form together a simple bond or a double bond with the carbon atoms bearing them.

Preferably, R$_4$ and R$_6$, R$_5$ and R$_7$, form together an aromatic cycle, p is 1 and q is 0, to constitute, for example, a derivative of the amino-indanol type.

Within the present invention:
an "aryl group" means preferably a mono- or polycyclic system possessing one or several aromatic nuclei among which can be mentioned the phenyl group, the naphtyl group, the tetrahydronaphtyl group, the indanyl group and the binaphtyl group. The aryl group may be substituted by 1 to 3 substituents chosen independently from each other among a hydroxyl group, a linear or branched alkyl group comprising 1 to 4 carbon atoms such as methyl, ethyl, propyl or preferably tert-butyl, a nitro group, a ($C_1$-$C_4$)alkoxy group and a halogen atom, such as chlorine, bromine or iodine, a "heteroaryl group" means preferably an aryl group comprising 1 to 3 heteroatoms, such as nitrogen, sulphur or oxygen, and as such heteroaryl group can be mentioned the pyridinyl, pyrazinyl, pyridazinyl, quinolyl, isoquinolyl groups, etc, a "heterocycle" or "heterocyclic group" means preferably a cycle with 5 or 6 members comprising from 1 to 3 heteroatoms such as sulphur, nitrogen and oxygen. This definition also comprises bicycles where a heterocyclic group such as previously defined is fused with a phenyl group, a cyclohexane group or another heterocycle. Among the heterocyclic groups can be mentioned imidazolyl, indolyl, isoxazolyl, furyl, pyrazolyl, thienyl, etc.

The ligand preferably used in the invention presents a constrained molecular structure, cyclic non aromatic, bearing the groups $G_1$ and $G_2$ and able to be fused with a cycle. The tests performed have shown that the conformation constraint of this type of ligand is a major parameter contributing to the enantioselectivity.

Thus, the optically active amino-alcohol used as a ligand in the present invention is preferably a beta-amino-alcohol of cis relative stereochemistry, such as (1R,2S)-cis-amino-indanol, 3-exo-dimethylaminoborneol and cis-2-amino-cyclopentanol, for example.

More particularly, the ligand of formula (III) may notably be (1S,2R)-(−)- or (1R,2S)-(+)-1-amino-2-indanol. Thus, the use of this ligand allows for the selective direction of the oxidation reaction of 5-methoxy-2-[[4-methoxy-3,5-dimethyl-2-pyridinyl)methyl]thio]imidazo[4,5-b]-pyridine, to selectively obtain S-tenatoprazole, as indicated here-after.

Under the operating conditions, the ligand forms an asymmetric complex with the metal catalyst where the metal is oxidised by the oxidizing agent.

According to an implementation of the method of the invention, the reaction is carried out in an organic solvent or in a mixture of solvents.

The organic solvent is preferably aprotic and polar, and may be selected from N-methyl-pyrrolidone (NMP), dimethyl-formamide (DMF), dimethylacetamide (DMA) and pyridine, alone or as a mixture of several. Unexpectedly, the tests performed have shown that these solvents, in the case of the asymmetric oxidation of sulphides comprising an imidazo-pyridinyl group, contribute to the enantioselectivity and limit the formation of sulfones.

The oxidation reaction is easily carried out at low temperatures or at room temperature. It may be more advantageous to perform the reaction at a temperature comprised between −10 and 30° C. and preferably between about 0 and 25° C. to contribute to the enantioselectivity. A higher temperature may cause a decrease in selectivity. For example, in the case of the preparation of tenatoprazole from the corresponding prochiral sulphide, in the presence of Ti(OiPr)$_4$ and of amino-indanol in NMP, the enantiomeric excess decreases from 97 to 66% when the temperature is brought up from 20 to 40° C. On the contrary, it goes up to 99% when operating at low temperatures close to 0° C.

Thus, the titanium/ligand catalytic system of the present invention is different from those of the known methods of the state of the art as far as the ligand used as well as the implementation of the oxidation reaction are concerned.

One of the advantages of the method of the invention is that the order of addition of the reagents and components of the reaction medium does not matter and has no notable incidence on the conversion rate or on the enantioselectivity. According to a preferred form of implementation of the method, the ligand and the titanium-based catalyst are set in solution in the solvent to form the titanium/ligand catalytic system, before adding the sulphide in solution in the same solvent and finally, the oxidant. According to another variation of the invention, the titanium/ligand catalytic system is added to sulphide in two steps, at the start of the reaction and during the reaction, that is to say that an extra addition of ligand and of titanium-based catalyst is performed during the reaction, possibly associated with an extra addition of oxidant.

The method of the invention is advantageously carried out in a solvent in neutral medium without requiring the addition of a base; however, working in an acid medium which might cause a degradation of the final product should be avoided. The tests conducted showed that the addition of a base to the reaction medium under the conditions of the method of the invention does not improve the enantioselectivity and tends to reduce the conversion rate of sulfoxide. Thus, the addition of di-isopropylethylamine reduces the conversion rate from above 60% down to about 40%. On the contrary, in a known method such as described in above-mentioned U.S. Pat. No. 5,948,789, the addition of a base such as triethylamine and N,N-di-isopropylethylamine improves the enantioselectivity of the reaction.

Besides, the oxidation reaction according to the invention does not require water as is generally the case to improve the performance of usual methods. Thus, the tests performed have demonstrated that, on the contrary, the addition of water has a negative impact on the selectivity of the reaction by contributing to the formation of sulfone, on the enantioselectivity by strongly reducing it, and on the conversion rate which dramatically drops down. More particularly, the tests conducted showed that the presence of water, without changing the other conditions, reduces the enantiomeric excess from 99% to about 60% whereas the sulfone content goes up to more than 7%.

Finally, the simplification of the operating conditions of the preparation of the titanium (IV)/amino-indanol complex plays a non negligible part in the advantages of the present invention. According to another form of the method of the invention, the preliminary complexation between titanium and the chiral ligand may be performed in the reaction medium at room temperature and does not require any preliminary ripening.

The method of the invention is particularly advantageous in as much as the oxidizing agent and the catalyst are widely available on the market at low costs and are easy to use. Moreover the catalyst may be used efficiently and in very small quantities. The yield obtained in enantiomer is excellent and, besides, the catalyst and the ligand can generally be recycled under good conditions without any decrease of the enantiomeric excess.

The method of the present invention is particularly advantageous in the case of the preparation of the enantiomers of tenatoprazole which can be represented by the following general formula:

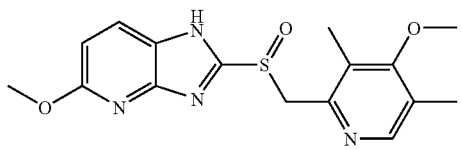

Therefore, for example, according to the method of the invention, an enantioselective oxidation of 5-methoxy-2-[[(4-methoxy-3,5-dimethyl-2-pyridinyl)methyl]thio]imidazo[4,5-b]-pyridine by cumene hydroperoxide or tert-butyl hydroperoxide in presence of Ti(OiPr)$_4$ and of amino-indanol in NMP can advantageously be carried out in order to obtain (−)-5-methoxy-2-[[(4-methoxy-3,5-dimethyl-2-pyridinyl)methyl]sulfinyl]imidazo[4,5-b]pyridine, that is to say tenatoprazole, the formula of which is represented above.

More particularly, it was observed that the above oxidation of sulphide allowed for the (−) enantiomer, of S configuration, to be obtained under excellent purity and yield conditions if a titanium-based catalyst was used in association with a ligand comprising (1R,2S)-cis-1-amino-indan-2-ol in a DMF, NMP, DMA or pyridine solution.

On the contrary, the (+) isomer, of R configuration, can also be obtained under excellent selectivity and yield conditions using (1S,2R)-cis-1-amino-indan-2-ol as a ligand.

The S and R enantiomers of tenatoprazole can be used under the form of salts, notably alkaline or alkaline earth metal salts, and for example under the form of sodium, potassium, lithium, magnesium or calcium salts. These salts can be obtained from the S or R enantiomer of tenatoprazole isolated beforehand, by salification reaction according to a usual method of the technique, for example by action of basic mineral reagents comprising alkaline or alkaline earth counter-ions.

The S enantiomer of tenatoprazole corresponds to (−)-5-methoxy-2-[[(4-methoxy-3,5-dimethyl-2-pyridinyl)methyl]sulfinyl]imidazo[4,5-b]pyridine, or (−)-tenatoprazole. This form can be determined by optical rotation measurements according to the usual techniques. Thus, the optical rotation angle of (−)-tenatoprazole is levogyrous in dimethylformamide, and its melting point is 130° C. (decomposition).

The S and R enantiomers of tenatoprazole, in the treatment of the diseases mentioned below, can be administered under the usual forms appropriate for the chosen mode of administration, for example per oral or parenteral route, preferably per oral or intravenous route.

For example, tablet or capsule formulations containing one or the other S and R enantiomers of tenatoprazole as active substance can be used, or even oral solutes, or emulsions or solutions for parenteral administration containing a tenatoprazole salt with a usual pharmaceutically acceptable medium. The tenatoprazole enantiomer salt may be chosen for example among sodium, potassium, lithium, magnesium or calcium salts.

The S and R enantiomers of tenatoprazole obtained according to the method of the present invention may be used in the manufacture of drugs for the treatment of digestive diseases, in particular those where an inhibition of the acid secretion must be strong and prolonged, for the treatment of the symptoms and lesions of the gastro-oesophageal reflux disease, of digestive haemorrhages resistant to other proton pump inhibitors.

The dosage is determined by the practitioner according to the condition of the patient and the severity of the disease. It is generally comprised between 10 and 120 mg, preferably between 20 and 80 mg, of S or R enantiomer of tenatoprazole per day.

Examples of enantiomer preparations are described hereafter so as to illustrate the present invention without limiting its scope.

Example 1

Preparation of (S)-(−)-tenatoprazole (1R,2S)-(+)-1-amino-2-indanol (22.8 mg, 0.151 mmol) and titanium isopropoxide (IV) (22 µl, 0.076 mmol) are set in solution in anhydrous NMP (0.65 mL).

A solution in NMP of 5-methoxy-2-[[(4-methoxy-3,5-dimethyl-2-pyridinyl)-methyl]thio]imidazo[4,5-b]pyridine (100 mg, 0.303 mmol) is then added to the above-mentioned complex under stirring at 20° C., immediately followed by cumene hydroperoxide (80%, 65 µl, 0.352 mmol).

The homogeneous mixture is maintained under stirring at 20° C. for 5 hours. The raw product contains 60% of sulphide, 2% of sulfone and 38% of sulfoxide with an enantiomeric excess (e.e.) of 95% (chiral HPLC analysis).

The enantiomeric excess is determined by high pressure liquid chromatography on a CHIRALPAK AS 10 µm (250× 4.6 mm) column at 30° C.

| | |
|---|---|
| Eluent: | n-heptane + 0.01% TFA/propan-2-ol (45:55) |
| Flow rate | 1 mL/min |
| Volume injected | 5 µL |
| Wavelength | 302 nm |
| Retention time of sulphide | 4.3 min |
| Retention time of the R-enantiomer | 6.7 min |
| Retention time of sulfone | 8.1 min |
| Retention time of the S-enantiomer | 11.8 min |
| $T_F$: | 129-130° C. |
| $[\alpha]^{20}_D$: | −186.6 (c 0.1, DMF) |

UV spectrum (methanol-water): $\lambda_{max}$: 272 nm ($\epsilon$=6180), 315 nm (e=24877).

Infra-red (K)Br): 3006, 1581, 1436, 1364, 1262, 1026, 1040 and 823 cm$^{-1}$.

NMR $^1$H (DMSO d$_6$) δ (ppm): 2.20 (s, 6H), 3.70 (s, 3H), 3.91 (s, 3H), 4.69-4.85 (m, 2H), 6.80 (d, J=8.5 Hz, 1H), 7.99 (d, J=8.5 Hz, 1H), 8.16 (s, H), 13.92 (s, 1H).

NMR $^{13}$C (DMSO d$_6$) δ (ppm): 13.2; 15.0; 56.6; 60.8; 62.6; 107.2; 129.5; 130.4; 131.9; 135.1; 150.5; 151.4; 156.9; 160.7; 163.0; 166.6.

Example 2

Preparation of (R)-(+)-tenatoprazole

The method of example 1 is repeated but (1R,2S)-(+)-1-amino-2-indanol is replaced with (1S,2R)-(−)-1-amino-2-indanol. The same oxidizing agent is applied to the same quantity of 5-methoxy-2-[[(4-methoxy-3,5-dimethyl-2-pyridinyl)methyl]thio]imidazo[4,5-b]pyridine as in example 1 and the same catalyst is used.

The physical and spectroscopic constants of (R)-tenatoprazole are identical to those of (S)-tenatoprazole, except for the specific rotatory power: $[\alpha]^{20}_D$: +185.9 (c 0.1, DMF).

Example 3

Preparation of (S)-Tenatoprazole (1R,2S)-(+)-1-amino-2-indanol (22.8 mg, 0.151 mmol) and titanium isopropoxide (IV) (22 µl, 0.076 mmol) are set in solution in DMF (1 volume). The solution is maintained at 0° C. for 30 minutes.

A solution in DMF (6 volumes) of 5-methoxy-2-[[(4-methoxy-3,5-dimethyl-2-pyridinyl)-methyl]thio]imidazo[4,5-b]pyridine (100 mg, 0.303 mmol) is added under stirring at 20° C., immediately followed by cumene hydroperoxide (80%, 65 µL, 0.352 mmol)

The homogeneous mixture is maintained under stirring at 0° C. for 6 hours. The raw product contains 60% of sulphide, 0.1% of sulfone and 39% of sulfoxide, with an enantiomeric excess (e.e.) of 99% (chiral HPLC analysis).

Example 4

Preparation of (S)-Tenatoprazole

The same method as described in Example 3 here-above is used, except that DMF is replaced by DMA.

The homogeneous mixture is maintained under stirring at 22° C. for 6 hours. The raw product contains 47% of sulphide, 0.5% of sulfone and 52% of sulfoxide, with an enantiomeric excess (e.e.) higher than 99% (chiral HPLC analysis).

Example 5

Preparation of (S)-Tenatoprazole 5-methoxy-2-[[(4-methoxy-3,5-dimethyl-2-pyridinyl)-methyl]thio]imidazo[4,5-b]pyridine (100 mg, 0.303 mmol) is solubilised in anhydrous DMF (0.65 mL). Titanium isopropoxide (IV) (22 µl, 0.076 mmol) and (1R,2S)-(+)-1-amino-2-indanol (22.8 mg, 0.151 mmol) in anhydrous DMF are added under stirring at 22° C., followed by cumene hydroperoxide (80%, 65 µL, 0.352 mmol).

The homogeneous mixture is maintained under stirring at 22° C. for 5 hours.

The raw product contains 61% of sulphide, 1% of sulfone and 38% of sulfoxide, that is to say S-tenatoprazole, with an enantiomeric excess (e.e.) of 98% (chiral HPLC analysis).

Example 6

Preparation of (S)-Tenatoprazole 5-methoxy-2-[[(4-methoxy-3,5-dimethyl-2-pyridinyl)-methyl]thio]imidazo[4,5-b]pyridine (100 mg, 0.303 mmol) and (1R,2S)-(+)-1-amino-2-indanol (22.8 mg, 0.151 mmol) are solubilised in anhydrous pyridine (0.65 mL); titanium isopropoxide (IV) (22 µL, 0.076 mmol) is added under stirring at 22° C., followed by cumene hydroperoxide (80%, 65 µL, 0.352 mmol).

The homogeneous mixture is maintained under stirring at 22° C. for 5 hours. The raw product contains 16% of sulphide, 4% of sulfone and 68% of sulfoxide with an enantiomeric excess (e.e.) of 97% (chiral HPLC analysis).

The enantiomeric excess is determined by high pressure liquid chromatography on a CHIRALPAK AS 10 µm (250× 4.6 mm) column at 30° C.

Example 7

Preparation of (S)-Tenatoprazole 5-methoxy-2-[[(4-methoxy-3,5-dimethyl-2-pyridinyl)-methyl]thio]imidazo[4,5-b]pyridine (100 mg, 0.303 mmol) is solubilised in anhydrous NPM (0.65 mL), to which (1R,2S)-(+)-1-amino-2-indanol (22.8 mg, 0.151 mmol) and titanium isopropoxide (IV) (22 µL, 0.076 mmol) are added under stirring at 22° C., followed by cumene hydroperoxide (80%, 65 µl, 0.352 mmol).

The homogeneous mixture is maintained under stirring at 22° C. for 5 hours. The raw product contains 56% of sulphur, 2% of sulfone and 42% of sulfoxide with an enantiomeric excess (e.e) of 95% (chiral HPLC analysis).

Example 8

Preparation of (S)-Tenatoprazole 5-methoxy-2-[[(4-methoxy-3,5-dimethyl-2-pyridinyl)-methyl]thio]imidazo[4,5-b]pyridine (0.4 g), 0.5 eq. of (1R,2S)-(+)-1-amino-2-indanol and 0.25 eq. (0.091 mL) of Ti(O-iPr)$_4$ are successively introduced in NPM under stirring, using a 100 µl glass syringe previously dried in the oven. To this solution is then added in one go, at 0° C. and over 30 seconds 1.16 eq. (0.26 mL) of cumene hydroperoxyde using a syringe (250 µl, glass, previously dried in the oven,).

The homogeneous solution is maintained under stirring at 0° C. for 6 hours. Using a syringe as indicated above, 0.25 eq. (0.091 mL) of Ti(OiPr)$_4$, 0.5 eq. of (1R,2S)-(+)-1-amino-2-indanol and 1.16 eq. (0.26 mL) of cumene hydroperoxide are successively added again over 30 seconds, in one go and at 0° C. The reaction medium is maintained under stirring at 0° C. for 1.75 hours and maintained for one night at 5° C. in a refrigerator. At the end of the reaction, the reaction medium is homogenous and sunset orange.

The raw product contains 0.5% of sulphur, 1% of sulfone and 90% of sulfoxide with an enantiomeric excess (e.e) higher than 99.5% (chiral HPLC analysis).

Example 9

Preparation of (S)-Tenatoprazole

The same method as described in Example 8 here-above is used except that NMP is replaced by DMF.

After 5 hours of reaction, (1R,2S)-(+)-1-amino-2-indanol (0.5 eq.), Ti(OiPr)$_4$ (0.25 eq.) and 1.16 eq. (0.26 mL) of cumene hydroperoxide are successively added again, in one go and at 0° C. using a 250 µl glass syringe previously dried in the oven, and the reaction medium is maintained under stirring at 0° C.

Samples are taken at 5 hours and 24 hours. At the end of the reaction, the reaction medium is homogeneous and sunset orange.

After 5H00 and before the addition, the raw product contains 62% of sulphur, 0.1% of sulfone and 38% of sulfoxide, with an enantiomeric excess (e.e) higher than 99.0% (chireal HPLC analysis).

After 24H00, the raw product contains 13% of sulphur, 2.5% of sulfone and 84% of sulfoxide with an enantiomeric excess (e.e) higher than 99.0% (chiral HPLC analysis).

Example 10

Preparation of (S)-Tenatoprazole

The same method as described in Example 9 here-above is used except that DMF is replaced by DMA.

After 5H00, and before the addition, the raw product contains 60% of sulphur, 0.8% of sulfone and 38% of sulfoxide, with an enantiomeric excess (e.e) higher than 99% (chiral HPLC analysis).

After 24H00, the raw product contains 3% of sulphur, 4.7% of sulfone and 90% of sulfoxide, with an enantiomeric excess (e.e) higher than 99.0% (chiral HPLC analysis).

Example 11

Preparation of (R)-Tenatoprazole

1. Preparation of endo-iso-borneol

In a 10 ml flask equipped with an addition ampoule, camphorquinone-3-oxime is dissolved in 4.5 mL of NaOH at 30%. The yellow suspension is cooled down to 0° C. and treated by adding zinc powder via the ampoule by small fractions and over 30 minutes.

The temperature is then maintained at 0° C. for another 10 minutes. The greyish-yellow suspension obtained is heated to 23° C. and maintained at this temperature for 15 minutes until the yellow colour has totally disappeared. The grey suspension is maintained under stirring at 23° C. for 5 minutes and is then extracted with 5 mL of methyl tert-butyl ether (MTBE). The organic phase is successively washed with 2×2.5 mL of water, dried on MgSO$_4$ and then concentrated until a volume of about 20 mL is obtained.

The solution is then added drop per drop via a burette to a solution of LiAlH$_4$ in 50 mL of MTBE, in a 250 mL flask equipped with a condenser, under nitrogen pressure and at 23° C. The grey suspension is heated up to 40° C. and maintained under stirring at 40° C. for 18 hours. The reaction medium is then cooled down to 0° C. and 2 mL of distilled water are added in such a way that the temperature does not exceed 5° C. The suspension is filtered on celite, washed with 40 mL of MTBE followed by 30 ml of water before it is dried on MgSO$_4$, filtered and concentrated to provide 0.65 g of white crystals.

isolated yield of 49%

Titre of 80% (cis/trans ratio of 5/1 based on NMR 1H).

Purification of endo-iso-borneol:

300 mg of white crystals are dissolved in 8.5 mL of HCl (6M) in a 25 mL flask. The solution is heated up to 100° C. and maintained under stirring at this temperature for 24 hours. The brown solution is washed with 4×8 mL of dichloromethane. The aqueous phase is basified by adding 5 mL of NaOH at 50% (pH=12), and extracted with 3×8 mL of MTBE. The organic phase is dried on MgSO$_4$, filtered and concentrated to obtain a brown solid which is sublimated at 80° C. under 1 mmHg.

120 mg of white crystals of titre 90% are obtained (the cis/trans ratio is of 10/1 based on NMR 1H). The structure was validated by mass spectrometry.

2. Preparation of (R)-tenatoprazole

Endo-iso-borneol (0.5 eq.) and titanium isopropoxide (IV) (0.25 eq.) are rapidly set in solution in NMP and added to 5-methoxy-2-[[(4-methoxy-3,5-dimethyl-2-pyridinyl)-methyl]thio]imidazo[4,5-b]pyridine (100 mg, 0.303 mmol). 5 s after the addition, cumene hydroperoxide (1.16 eq.) is added in 2 seconds. The mixture is maintained under stirring at 20° C. for hours.

The raw product contains 71% of sulphur, 5% of sulfone and 24% of sulfoxide, with an enantiomeric excess (e.e) of 20% (R enantiomer) (chiral HPLC analysis).

The invention claimed is:

1. Method for the enantioselective preparation of sulfoxide derivatives or of their salts, represented by the following formula:

A—CH$_2$—SO—B  (Ia)

in which A is a pyridinyl nucleus diversely substituted and B a heterocyclic residue comprising an imidazo-pyridinyl nucleus, wherein an enantioselective oxidation of a sulphide of the following general formula (I) is performed

A—CH$_2$—S—B  (I)

in which A and B have the above-mentioned meanings, using an oxidizing agent in the presence of a titanium(IV)-based catalyst and a chiral ligand comprising a cyclic beta- or gamma-amino-alcohol, in solution in a polar aprotic solvent selected from the group consisting of N-methyl-pyrrolidone (NMP), dimethylformamide (DMF), dimethylacetamide (DMA), pyridine, and mixtures thereof, followed as necessary by a salification by a base.

2. Method according to claim 1, wherein in general formula (I), A represents a pyridinyl group or a pyridinyl group bearing one or several substituents selected from the group consisting of linear or branched alkyl group of 1 to 6 carbon atoms, linear or branched alkoxy groups of 1 to 6 carbon atoms, methyl or ethyl groups substituted by one or several halogen atoms, amino, alkylamino or dialkylamino groups where the alkyl moiety is linear or branched and comprises 1 to 5 carbon atoms; B represents an imidazo-[4,5-b]-pyridinyl heterocycle, optionally substituted by one or several linear or branched alkyl groups of 1 to 6 carbon atoms, or linear or branched alkoxy groups of 1 to 6 carbon atoms.

3. Method according to claim 2, wherein groups A and B are substituted on one or several carbons by a methyl, ethyl, methoxy or trihalogenomethyl group.

4. Method according to claim 3, wherein A is a 2-pyridinyl group substituted by one or several methyl, ethyl, methoxy of trifluoromethyl groups.

5. Method according to claim 3, wherein A is a 4-methoxy-3,5-dimethyl-2-pyridinyl group and B is a 5-methoxy-imidazo-[4,5-b]-pyridinyl group.

6. Method according to claim 1, wherein the enantiomer obtained is salified by action of basic mineral reagents comprising alkaline or alkaline earth counter ions.

7. Method according to claim 6, wherein the salt is a sodium, potassium, lithium, magnesium or calcium salt.

8. Method according claim 1, wherein the oxidizing agent is a hydroperoxide.

9. Method according to claim 8, wherein the oxidizing agent is cumene or tertbutyl hydroperoxide.

10. Method according to claim 1, wherein the oxidizing agent is hydrogen peroxide at a minimum of 30%, or hydrogen peroxide complexed with urea (UHP), and the reaction medium is supplemented with a dehydrating agent or an appropriate molecular sieve.

11. Method according to claim 1, wherein the catalyst is a titanium complex.

12. Method according to claim 11, wherein the titanium complex is titanium isopropoxide of titanium acetylacetonate.

13. Method according to claim 1, wherein the ligand is a cyclic beta- or gamma-amino-alcohol represented by the following general formula (II):

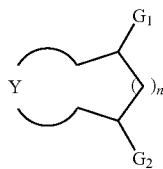

II in which $G_1$ represents an amino group —$NR_1R_2$ or an imino group —N=$CR_1R_2$ and $G_2$ represents an —$OR_3$ group, or the reverse; n equals 0 or 1; $R_1$ and $R_2$ are identical or different and are independently selected from the group consisting of a hydrogen atom, a linear or branched alkyl group of 1 to 6 carbon atoms, an aryl, heteroaryl, and acyl of sulfonyl group, $R_3$ represents a hydrogen atom, a linear or branched alkyl group of 1 to 6 carbon atoms or an aryl or heteroaryl group, and Y is a cyclic residue.

14. Method according to claim 13, wherein the cyclic amino-alcohol is represented by the following formula (III)

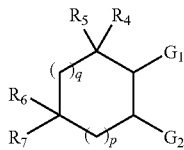

III in which $G_1$ and $G_2$ have the above-mentioned definitions; p and q are identical or different and equal 0, 1 or 2; $R_4$, $R_5$, $R_6$ and $R_7$ are identical or different and represent a hydrogen atom or a linear or branched alkyl group of 1 to 6 carbon atoms, $R_4$ and $R_6$, and/or $R_5$ and $R_7$, being able to form together an aliphatic, aromatic or heteroaromatic cycle, and $R_5$ and $R_7$ being able to form together a simple bond or a double bond with the carbon atoms bearing them.

15. Method according to claim 14, wherein $R_4$ and $R_6$, $R_5$ and $R_7$, form together an aromatic cycle to constitute a derivative of the amino-indanol type.

16. Method according to claim 13, wherein the ligand is (1S,2R)-(−)- or (1R,2S)-(+)-1-amino-2-indanol, 3-exo-dimethylaminoborneol or cis-2-amino-cyclo-pentanol.

17. Method according to claim 1, wherein the titanium/ligand catalytic system is added to sulphur in two steps, at the start of the reaction and during the reaction, the second step being optionally associated with a new addition of oxidant.

18. Method according to claim 1, wherein an enantioselective oxidation of 5-methoxy-2-[[(4-methoxy-3,5-dimethyl-2-pyridinyl)methyl]thio]imidazo[4,5-b]pyridine is performed in order to obtain (−)-5-methoxy-2-[[(4-methoxy-3,5-dimethyl-2-pyridinyl)methyl]sulfinyl]imidazo[4,5-b]pyridine using a titanium-based catalyst associated to a ligand constituted by (1R,2S)-1-[2-hydroxy-3,5-di-tert-butyl-benzylidene)-amino]-indan-2-ol.

19. Method according to claim 18, wherein the oxidation reaction is carried out in a solvent, in neutral medium.

20. Method according to claim 1, wherein the reaction is carried out at a temperature comprised between −10 and 30° C.

21. Method according to claim 19, wherein the reaction is carried out at a temperature comprised between −10 and 30° C.

* * * * *